US010321687B2

(12) United States Patent
Noga

(10) Patent No.: US 10,321,687 B2
(45) Date of Patent: Jun. 18, 2019

(54) *CONIOTHYRIUM MINITANS* FOR USE AGAINST MOSS GROWTH

(71) Applicant: Bayer CropScience Aktiengesellschaft, Monheim am Rhein (DE)

(72) Inventor: Sandra Noga, Leverkusen (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/736,448

(22) PCT Filed: Jun. 28, 2016

(86) PCT No.: PCT/EP2016/064968
§ 371 (c)(1),
(2) Date: Dec. 14, 2017

(87) PCT Pub. No.: WO2017/001383
PCT Pub. Date: Jan. 5, 2017

(65) Prior Publication Data

US 2018/0177195 A1 Jun. 28, 2018

(30) Foreign Application Priority Data

Jul. 2, 2015 (EP) .................................... 15174941

(51) Int. Cl.
| | |
|---|---|
| *A01N 25/08* | (2006.01) |
| *A01N 33/12* | (2006.01) |
| *A01N 35/02* | (2006.01) |
| *A01N 35/06* | (2006.01) |
| *A01N 37/34* | (2006.01) |
| *A01N 37/46* | (2006.01) |
| *A01N 43/82* | (2006.01) |
| *A01N 47/14* | (2006.01) |
| *A01N 59/16* | (2006.01) |
| *A01N 59/20* | (2006.01) |
| *A01N 63/04* | (2006.01) |
| *A01N 43/653* | (2006.01) |

(52) U.S. Cl.
CPC ............ *A01N 63/04* (2013.01); *A01N 25/08* (2013.01)

(58) Field of Classification Search
CPC ................................ A01N 63/04; A01N 25/08
See application file for complete search history.

(56) References Cited

U.S. PATENT DOCUMENTS 5,766,583 A * 6/1998 Luth ..................... A01N 63/04 424/93.5
2011/0257009 A1* 10/2011 Seitz ..................... A01N 43/90 504/100

FOREIGN PATENT DOCUMENTS

| | | | | |
|---|---|---|---|---|
| DE | 4139074 A1 | 6/1993 | | |
| FR | 2975568 A1 | 11/2012 | | |
| WO | 96/21358 A1 | 7/1996 | | |
| WO | 02/13615 A1 | 2/2002 | | |
| WO | 2005/077172 A1 | 8/2005 | | |
| WO | WO-2013110591 A1 * | 8/2013 | ............ | A01N 43/40 |

OTHER PUBLICATIONS

Tomprefa, N., et al., "Antimicrobial Activity of Coniothyrium minitans and Its Macrolide Antibiotic Macrosphelide A," Journal of Applied Microbiology, 2009, vol. 106, pp. 2048-2056.
International Search Report and Written Opinion on the International Searching Authority, PCT International Patent Application No. PCT/EP2016/064968, dated Aug. 11, 2016, 10 pages.

* cited by examiner

*Primary Examiner* — John Pak
*Assistant Examiner* — Nathan W Schlientz
(74) *Attorney, Agent, or Firm* — Adam L. Lunceford; Michelle L. Samonek

(57) ABSTRACT

The invention relates to the use of *Coniothyrium minitans* for controlling moss growth and to a method of controlling moss growth, comprising applying *Coniothyrium minitans* to an area to be kept free from mosses.

15 Claims, No Drawings

CONIOTHYRIUM MINITANS FOR USE AGAINST MOSS GROWTH

CROSS-REFERENCE TO RELATED APPLICATION (S) The present application is a 35 U.S.C. § 371 national phase entry of International Application No. PCT/EP2016/064968, filed Jun. 28, 2016, which claims the benefit under 35 U.S.C. § 119 of European Patent Application No. 15174941.3, filed Jul. 2, 2015, the entire contents of which are hereby incorporated herein by reference.

Moss growth is in a number of places considered to be a nuisance and in many places unwelcome, for example on turfed areas or on trees and on asphalted or cobbled ground or otherwise paved ground and on the roofs of houses.

Methods for controlling moss growth include physical removal and chemical treatment or a combination of these methods. Chemical methods, in particular, frequently have side effects such as, for example, damage to other plants, staining, corrosion or pollution of the air and/or water (Davison and Byther, 1999; Algae, Lichens and Mosses on Plants. Pacific Northwest Plant Disease Control Handbook. p. 39). Moreover, the efficacy of many herbicides against mosses has not been studied thoroughly. Finally, the safety regulations to be adhered to also make the handling, dosing and storing of chemical products more complex.

The fungus *Coniothyrium minitans* was identified firstly in 1947 and can be found in soils worldwide. It attacks sclerotia (overwintering structures or survival structures) of *Sclerotinia sclerotiorum* and *Sclerotinia minor*, other *Sclerotinia* species and *Sclerotium cepivorum* and destroys them. These plant pathogens have a range of host plants, especially including useful plants, where they cause considerable damage.

In view of the possibilities for controlling moss, which are not optimal, and the intended reduction of water and air pollution by herbicides, alternative and less harmful methods for controlling mosses should be found.

This technical problem is solved by the present invention as defined in the claims.

The present invention relates to the use of *Coniothyrium minitans* for controlling or preventing moss growth, for example in crops of useful plants or in places such as paved places where moss growth is undesired.

*Coniothyrium minitans* has as yet only been known as a biological fungicide which acts against *Sclerotinia* species. In the context of the present invention, however, it has been found that the fungus also inhibits moss growth and/or causes existing moss to die. It is to be noted that the effect can indeed be attributed to the fungus and not, for example, to the presence of formulation aids (see example).

In accordance with the invention, all strains belonging to the species *Coniothyrium minitans* can be used which have moss-growth-inhibiting or moss-controlling properties.

An especially preferred strain of *Coniothyrium minitans* is CON/M/91-08 (described in WO 96/21358), which has been deposited at the Deutsche Sammlung für Mikroorganismen and Zellkulturen in Braunschweig under the accession number DSM9660. The strain is used as biological plant protection agent against the fungi *Sclerotinia sclerotiorum* and *Sclerotinia minor*, which are causative organisms of white mould, and is commercially available under the trade name Contans®.

*Coniothyrium minitans* strain CON/M/91-08, like other *Coniothyrium minitans* strains, may be cultured as described for example in WO 96/21358, which is herewith incorporated by reference. For example, *Coniothyrium minitans* can be cultured on suitable substrates such as, for example, seeds of cereals, bran, straw or other plant matter, or else with the aid of agar culture medium conventionally used in fungal culture, for example potato dextrose agar or malt peptone agar, or on suitable support materials to which a culture medium has been added; and also in liquid nutrient media without the use of agar.

Usually, the strain is formulated on a carrier, preferably a water-soluble sugar carrier. The water-soluble carrier is preferably glucose or dextrose.

Besides *Coniothyrium minitans* CON/M/91-08, mutants of this strain which have the same properties in respect of moss growth as CON/M/91-08 are also encompassed.

Mosses are green terrestrial plants which can be divided into hornworts, liverworts and Bryophyta. *Coniothyrium minitans* is active against mosses in general, but in particular against Bryophyta such as, for example, haircap mosses.

Mosses sometimes grow in places where useful plants or ornamentals are being grown. To be mentioned here in particular is turf as found in parks, golf courses, sports grounds or in gardens. Turf is also frequently sold as turf rolls or turf sods, likewise susceptible to moss growth.

Other places where moss growth is undesired are certain areas or places, including paved areas or places, such as, for example, tiled, cobbled or asphalted areas, where mosses colonize joints or undesired gaps.

In a preferred embodiment, spores of *Coniothyrium minitans* are used.

Spores formed by *Coniothyrium minitans* are conidia (asexually formed spores), which are formed in pycnidia and are also referred to as pycnidiospores or pycnospores.

In a further preferred embodiment, the use takes place on turf.

In a further preferred embodiment, the use according to the invention takes place in gardens, parks, sport grounds, terraces, pavements and otherwise plant-free places.

In yet another preferred embodiment, the use takes place in combination with at least one herbicide which is preferably active against mosses.

In a further preferred embodiment, the herbicide is selected from the group consisting of dodecyldimethylammonium chloride, ACN (2-amino-3-chloro-1,4-naphtoquinone), carfentrazone-ethyl, lauroyl methyl-[beta]-alanine-sodium, ferrous ammonium sulphate, copper hydroxide, mancozeb, propineb, oxadiazone, formaldehyde and chlorothalonil.

In a further especially preferred embodiment, the use according to the invention takes place with at least one herbicide, simultaneously or alternatingly.

In a preferred embodiment, the application rate is between 2 and 2000 kg/ha. Preferred ranges comprise an application rate of between approximately 10 and approximately 500 kg/ha, furthermore preferred between approximately 20 and 200 kg/ha, for example 30, 40, 50, 100 or 150 kg/ha.

In a further preferred embodiment, the spore concentration in the formulation applied is between $1\times10^{8}$ and $1\times10^{10}$ /g.

The spores may be present in a concentration of between about $1\times10^{7}$ and about $1\times10^{15}$ spores/g carrier, preferably between about $1\times10^{8}$ and about $1\times10^{13}$ spores/g carrier. The most preferred concentration is between about $1\times10^{8}$ and about $1\times10^{10}$ spores/g carrier, for example about $1\times10^{9}$ spores/g carrier.

In another preferred embodiment, the use according to the invention is preventive.

In a further aspect, the invention relates to a method of controlling mosses, comprising applying *Coniothyrium* minitans to an area to be kept free from mosses, such as, for example, a crop of useful plants or places such as paved places.

To describe the preferred embodiments of this aspect of the invention, those of the first aspect of the invention may be used.

In a preferred embodiment, *Coniothyrium minitans* strain CON/M/91-08 is used.

In a preferred embodiment of the method according to the invention, spores of *Coniothyrium minitans* are used.

In a further preferred embodiment, the application takes place onto and/or into the soil or the area to be treated.

In a further preferred embodiment the application is effected on turf.

In a further preferred embodiment, the method according to the invention is applied in gardens, parks, sports grounds, terraces, pavements and otherwise plant-free places.

In a further preferred embodiment, the application of *Coniothyrium minitans* takes place in combination with at least one herbicide which is active against mosses.

In an especially preferred embodiment, the herbicide is selected from the group consisting of dodecyldimethylammonium chloride, ACN (2-amino-3-chloro-1,4-naphtoquinone), carfentrazone-ethyl, lauroyl methyl-[beta]-alanine-sodium, ferrous ammonium sulphate, copper hydroxide, mancozeb, propineb, oxadiazone, formaldehyde and chlorothalonil.

In a further especially preferred embodiment, the application of *Coniothyrium minitans* and at least one herbicide takes place simultaneously or alternatingly.

In a preferred embodiment of the method according to the invention, the application rate is between 2 and 2000 kg/ha.

In a further preferred embodiment, the spore concentration in the formulation applied is between $1 \times 10^7$ and $1 \times 10^{10}$ /g.

In another preferred embodiment, the method according to the invention is preventive.

The examples which follow describe the invention in non-limiting form.

EXAMPLE 1

Drench Test

The test was carried out under greenhouse conditions.

120 ml of a mixture of steamed field soil and sand (1:1) was filled into transparent cylindrical vessels 5.5 cm in size.

The test formulation, the product Contans®, comprising $1 \times 10^9$ spores of the strain *Coniothyrium minitans* CON/M/91-08, was dissolved in water and diluted with water to the desired concentrations. 20 ml of the made-up solutions were pipetted onto the soil in the vessels.

The vessels were covered with a transparent lid.

The vessels remained in the greenhouse for the next 19 weeks, at 15° C. and at natural light conditions. The lids were opened slightly after approximately 2 weeks, and the soil was watered every 3 weeks and kept moist.

The evaluation was effected by estimating, per vessel, the soil surface area which had in the meantime been covered by growth, predominantly haircup moss growth. 0% means an efficacy which corresponds to that of the untreated control, while an efficacy of 100% means that no moss growth was discernible.

In this test, the following formulations display an efficacy of up to 100% at a dose of 200 kg/ha (see table 1).

TABLE 1

|  | Concentration | Efficacy % |
| --- | --- | --- |
| Control |  | 0* |
| Contans ** | 2 kg/ha = 0.024 mg/ml | 50 |
| Contans** | 20 kg/ha = 0.24 mg/ml | 38 |
| Contans** | 200 kg/ha = 2.4 mg/ml | 100 |
| Glucose | 200 kg/ha = 2.4 mg/ml | 13 |
| DDAC-C10*** | 6.25 kg/ha = 20 μl/ml | 100 |

The *Coniothyrium minitans* spores used are bound to glucose. To rule out a potential effect of glucose on the moss growth, an experiment with glucose was carried out, and this experiment shows that the effect cannot be attributed to the glucose.

The invention claimed is:

1. A method of controlling moss growth, comprising applying *Coniothyrium minitans* to an area to be kept free from mosses;
    wherein the area to be kept free from mosses is a plant-free place.
2. The method according to claim 1, wherein spores of *Coniothyrium minitans* are used.
3. The method according to claim 1, wherein the application takes place onto a roof of a house.
4. The method according to claim 1, wherein the application is effected on a paved area or place where mosses have a tendency to colonize joints or undesired gaps.
5. The method according to claim 4, wherein the paved area or place is tiled, cobbled or asphalted.
6. The method according to claim 1, wherein the application of *Coniothyrium minitans* takes place in combination with at least one herbicide which is active against mosses.
7. The method according to claim 6, wherein the herbicide is selected from the group consisting of dodecyldimethylammonium chloride, ACN (2-amino-3-chloro-1,4-naphthoquinone), carfentrazone-ethyl, lauroyl methyl-[beta]-alanine-sodium, ferrous ammonium sulfate, copper hydroxide, mancozeb, propineb, oxadiazone, formaldehyde and chlorothalonil.
8. The method according to claim 6, wherein the application of *Coniothyrium minitans* and at least one herbicide takes place simultaneously or alternatingly.
9. The method according to claim 1, wherein the *Coniothyrium minitans* is applied in a formulation comprising between about $1 \times 10^7$ and about $1 \times 10^{15}$ spores *Coniothyrium minitans* per gram of formulation, and the formulation application rate is between 2 and 2000 kg/ha.
10. The method according to claim 9, wherein the formulation comprises between $1 \times 10^7$ and $1 \times 10^{10}$ spores *Coniothyrium minitans* per gram of formulation.
11. The method according to claim 1, wherein the *Coniothyrium minitans* is *Coniothyrium minitans* CON/M/91-08 with Accession Number DSM9660 or a mutant thereof having the same properties in respect of moss growth.
12. The method according to claim 1, wherein the *Coniothyrium minitans* is formulated on a carrier.
13. The method according to claim 12, wherein the carrier is glucose or dextrose.
14. The method according to claim 12, wherein the *Coniothyrium minitans* is formulated as spores on the carrier at a concentration of between about $1 \times 10^7$ and about $1 \times 10^{15}$ spores/g carrier.
15. The method according to claim 1, wherein the *Coniothyrium minitans* is applied as a drench.

* * * * *